United States Patent
Raff et al.

[11] Patent Number: 5,053,130
[45] Date of Patent: Oct. 1, 1991

[54] DIFFUSION AND/OR FILTRATION APPARATUS

[75] Inventors: Manfred Raff, Bisingen/Thanheim; Kurt Spranger, Ammerbuch/Entirgen, both of Fed. Rep. of Germany

[73] Assignee: Gambro Dialysatoren GmbH & Co. KG, Fed. Rep. of Germany

[21] Appl. No.: 237,504

[22] Filed: Aug. 26, 1988

[30] Foreign Application Priority Data

Aug. 31, 1987 [SE] Sweden .......................... 8703368-4

[51] Int. Cl.$^5$ ............................................. B01D 63/04
[52] U.S. Cl. .......................... 210/321.79; 210/321.88; 55/158
[58] Field of Search ...................... 210/321.65, 321.69, 210/321.71, 321.78, 321.79, 321.87, 321.88; 55/158

[56] References Cited

U.S. PATENT DOCUMENTS

| | | | |
|---|---|---|---|
| 4,219,426 | 8/1980 | Spekle et al. | 210/232 |
| 4,269,712 | 5/1981 | Hornby et al. | 210/321.3 |
| 4,289,623 | 9/1981 | Lee | 210/321.78 |
| 4,334,993 | 6/1982 | Norton | 210/321.3 |
| 4,480,683 | 11/1984 | Wollbeck et al. | 165/70 |
| 4,623,460 | 11/1986 | Kuzumoto et al. | 210/321.87 |
| 4,657,743 | 4/1987 | Kanno | 210/321.78 |
| 4,744,900 | 5/1988 | Bratt | 210/321.87 |
| 4,855,058 | 8/1989 | Halland et al. | 210/321.87 |

FOREIGN PATENT DOCUMENTS

| | | |
|---|---|---|
| 59-136104 | 4/1984 | Japan . |
| 61-141904 | 6/1986 | Japan . |
| 1175689 | 12/1969 | United Kingdom . |
| 2053725 | 2/1981 | United Kingdom . |

Primary Examiner—Robert A. Dawson
Assistant Examiner—Wanda L. Millard
Attorney, Agent, or Firm—Lerner, David, Littenberg, Krumholz & Mentlik

[57] ABSTRACT

The present invention relates to a diffusion and/or filtration apparatus, including a housing which consists of a cylindrical open-ended main part closed by two end caps and provided with an inlet and an outlet for a fluid. This fluid is adapted to flow through the fibers of a bundle of semipermeable hollow fibers which are arranged between two end walls within the housing. Additionally, the housing includes at least a second outlet for another fluid, with this fluid being adapted to be removed from the space outside the fibers through this second outlet, the ends of the hollow fibers being moulded into the end walls of the housing and opened by a cutting.

50 Claims, 3 Drawing Sheets

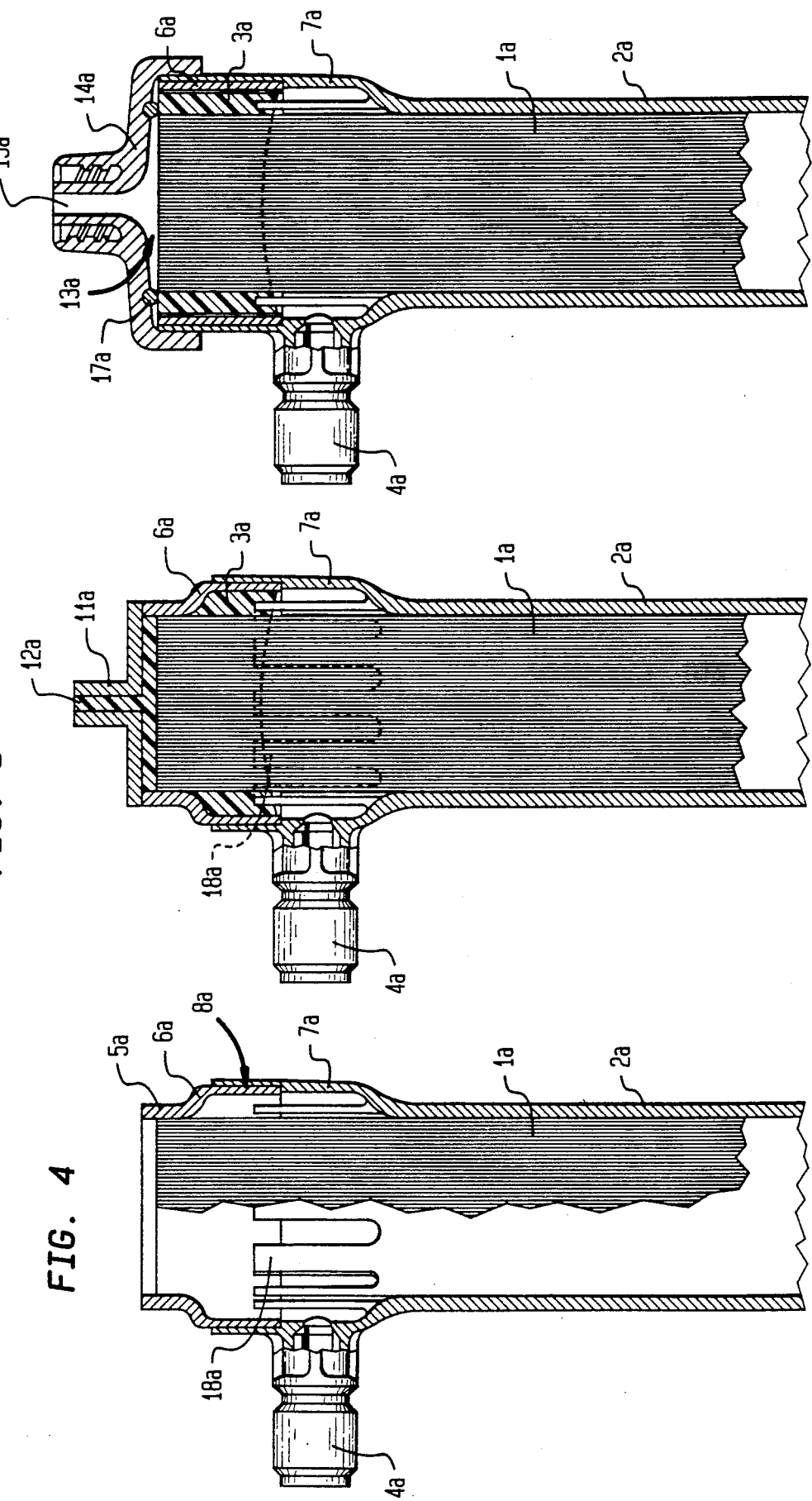

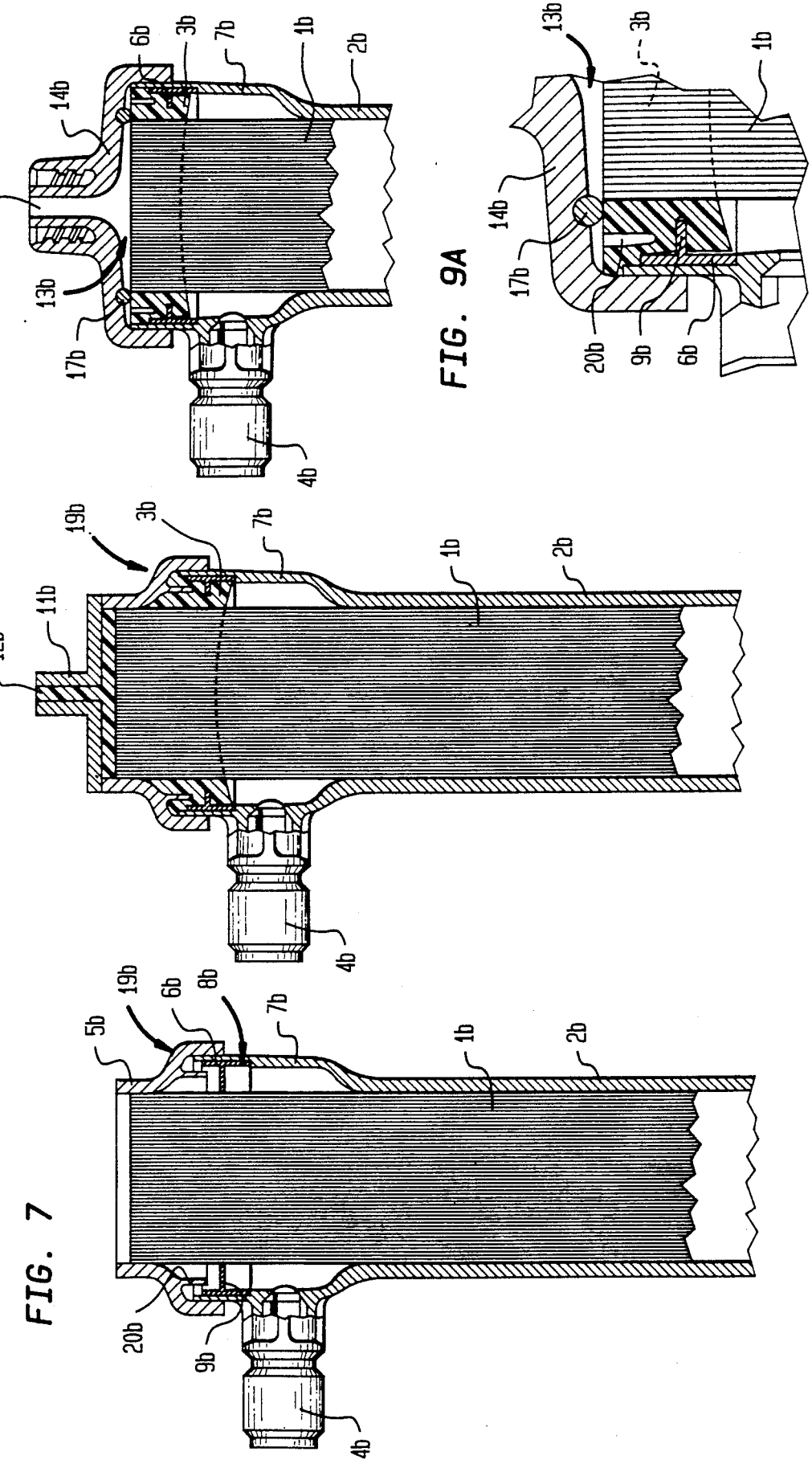

DIFFUSION AND/OR FILTRATION APPARATUS

FIELD OF THE INVENTION

The present invention relates to diffusion and/or filtration apparatus. More particularly, the present invention relates to such apparatus which includes a housing with a cylindrical open-ended main housing with a bundle of semi-permeable hollow fibers with end caps providing inlets and outlets for a first fluid which flow through the fibers and at least one other outlet for a second fluid which is withdrawn for the space between the fibers and the housing. Still more particularly, the present invention relates to methods of manufacturing such diffusion and/or filtration apparatus.

BACKGROUND OF THE INVENTION

Diffusion/filtration devices are used for various kinds of medical treatments, such as hemodialysis, hemofiltration, plasmapheresis and immunotherapy. Other fields of use include, inter alia, dialysis in general and filtration in general, for example in connection with the cleaning or desalination of sea water.

During the production of such diffusion/filtration devices each end of the housing, with a bundle of fibers therein, is normally enclosed in a casting mould into which the potting material for the adjacent end walls is fed in a liquid condition penetrating into and around the fibers. The penetration is controlled by the casting so that the penetration into the fibers is less than that around the fibers, making it possible to open the ends of the fibers by making a cut between the respective penetration depths.

These penetration depths may be controlled in different ways. Preferably, though, it is controlled in accordance with the method described and claimed in EP-B-O 165 478. Thus, the wall material may be fed into the device as described in the above European patent or, in the alternative, through the other two normally existing inlets/outlets as described in U.S. Pat. Nos. 4,227,295 or 4,329,229. In both cases, though, the wall material is firmly attached to the inside wall of the housing.

As a result, during the curing of the wall material, stresses develop which sometimes result in unacceptable cracks in the wall or the housing. Such cracks may for instance be created in connection with the opening of the fiber ends, the flushing of the apparatus or the sterilization of the completed apparatus.

An attempt to solve the above problem is described and claimed in U.S. Pat. No. 4,334,993. The present invention provides an alternative and novel solution for the same problem. Furthermore, the present invention provides additional advantages as described below.

SUMMARY OF THE INVENTION

The present invention relates to a diffusion and/or filtration apparatus of the kind defined above. This apparatus is characterized by the strength of the attachment between the moulded end walls and the housing being reduced or substantially eliminated by a ring which has a low adhesive capacity in relation to the material of the end walls. Additionally, in accordance with this invention, the end walls are also supported in the longitudinal direction of the housing.

Specifically, the present invention provides a housing that defines a longitudinally extending internal chamber which includes a first end and a second end. A bundle of semipermeable hollow fibers are disposed within the internal chamber. Accordingly, the hollow fibers extend longitudinally from the first end of the housing to the second end of the housing and therefore, have their own first and second end. These hollow fibers additionally have an outer surface.

Disposed between the bundle of hollow fibers and the housing is an end wall. This end wall sealingly separates the first and second ends of the hollow fibers from the outer surface of those hollow fibers.

Disposed at the first end of the housing is a first inlet. Disposed at the second end of the housing is a first outlet. Additionally, a second outlet is provided for the evacuation of fluid from the internal chamber of the housing at a point between the first and second ends of the housing.

Interposed between the end wall and the housing is a ring member. This ring member has a shape that corresponds to the housing and defines a cavity between itself and the hollow fibers. This ring member has a coefficient of adhesion in relation to the end wall which is lower than the coefficient of adhesion in relation to the housing. As a result, the structural integrity of the housing and the seal created by the end wall is enhanced and the risk of cracks therein is substantially eliminated.

As a result of the above defined structural integrity, a diffusion/filtration appartus in accordance with the present invention may even be heat sterilized (such as by means of a method according to U.S. Pat. No. 4,609,728) in dry condition, if suitable materials are chosen in light of the requirements involved. From the following description, it will be seen that an effective seal between the two fluids involved is also provided.

Additionally, longitudinal support of the end walls is preferably provided by a flange arranged on the ring. Such a flange may, for example, be arranged on the inside of the ring penetrating into the periphery of the end walls. Such construction may also be used for supporting the fiber bundle before the casting of the end walls. In the alternative, the ring may have include a protuberance which provides a support for the bundle of hollow fibers, especially before the molding of the end walls.

The ring may be supported in the longitudinal direction by the housing, preferably by being arranged in a groove in the inside wall of the housing.

This ring is also preferably extended outside of the housing prior to the cutting, in order to serve as a part of the mold for the potting material which will make up the end walls. This extended portion is cut together with the fibers in connection with the opening of the fiber ends.

In a preferred embodiment of the apparatus according to the instant invention, a second ring may be arranged at the outer end surfaces of the end walls which will result in a groove in each of the end surfaces. As with the other ring member, this ring has a low adhesive capacity in relation to the material of the end walls.

Alternatively, the longitudinal support of the ring may be provided by the housing itself, in that longitudinally extending tongues which are integral with the housing are partly moulded into the end walls. By such a construction the ring may be given a very simple form.

The present invention also relates to a method of manufacturing an apparatus as described above. This method includes a bundle of semipermeable hollow fibers being arranged in the cylindrical open ended main part of a housing, with the hollow fibers being supported by a ring having a low adhesive capacity in relation to the material of the end walls. This ring extends beyond the open ends of the hollow fibers and serves as an inlet and/or outlet for a flushing fluid for the flushing of the inside and the outside of the fibers. Additionally, the ring is thereafter used as a part of a mold for the introduction of a potting material that will form end walls. Thereafter, the housing, the fibers and the end walls are cut transverse the longitudinal orientation of the fibers and the housing in order to open the fiber ends, whereupon the apparatus finally is provided with end caps.

Specifically, the method of manufacture of the instant invention comprises the steps of providing a bundle of semipermeable hollow fibers. This bundle of hollow fibers has a first end and a second end. A housing which defines a longitudinally extending internal chamber that includes a first end and a second end and first outlet means for the evacuation of the internal chamber is also provided. The bundle of hollow fibers is then inserted into the internal chamber of the housing.

A ring member is also provided. This ring member is inserted into the internal chamber and over the hollow fibers. Further, this ring member as thus applied includes a portion that extends beyond the hollow fibers and thus forms an inlet.

A predetermined quantity of a potting material which has a lower coefficient of adhesion in relation to the ring member than its coefficient of its adhesion in relation to the housing, is then introduced through the inlet defined by the ring member. This potting material is allowed to penetrate to a predetermined depth of the internal chamber. As a result, the potting material seals the internal chamber from the ends of the housing and the ends of the hollow fibers. The housing, the ring member, and the hollow fibers are then cut transverse to the longitudinal line as defined by the internal chamber. This cut is made at a predetermined point between the inlet and the depth of penetration of the potting material. Lids are then attached to the first and seconds ends of the housing.

BRIEF DESCRIPTION OF DRAWINGS

FIG. 4 is a partial, side, elevational, partially sectional view of another diffusion and/or filtration apparatus of the present invention at a first stage of its manufacture;

FIG. 5 is a partial, side, elevational, partially sectional view of the apparatus of FIG. 4 at a second stage of its manufacture;

FIG. 6 is a partial, side, elevational, partially sectional view of the appratus of FIG. 4 at a final stage of its manufacture;

FIG. 7 is a partial, side, elevational, partially sectional view of another diffusion and/or filtration apparatus of the present invention at a first stage of its manufacture;

FIG. 8 is a partial, side, elevational, partially sectional view of the apparatus of FIG. 7 in a second stage of its manufacture;

FIG. 9 is a partial, side, elevational view of a portion of the apparatus of FIG. 7 in a final stage of its manufacture; and FIG. 9a is inlayed, a partial, side, elevational, sectional view of a portion of the apparatus of FIG. 9.

DETAILED DESCRIPTION

Figure 3:
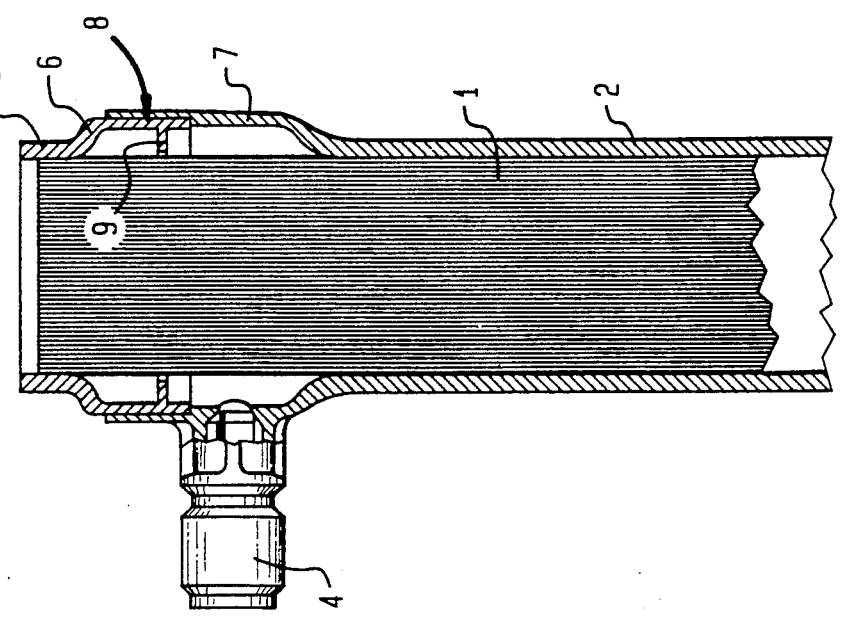
FIG. 3 is a partial, side, elevational, partially sectional view of the apparatus of FIG. 2 at a final state of its manufacture.
Figure 2:
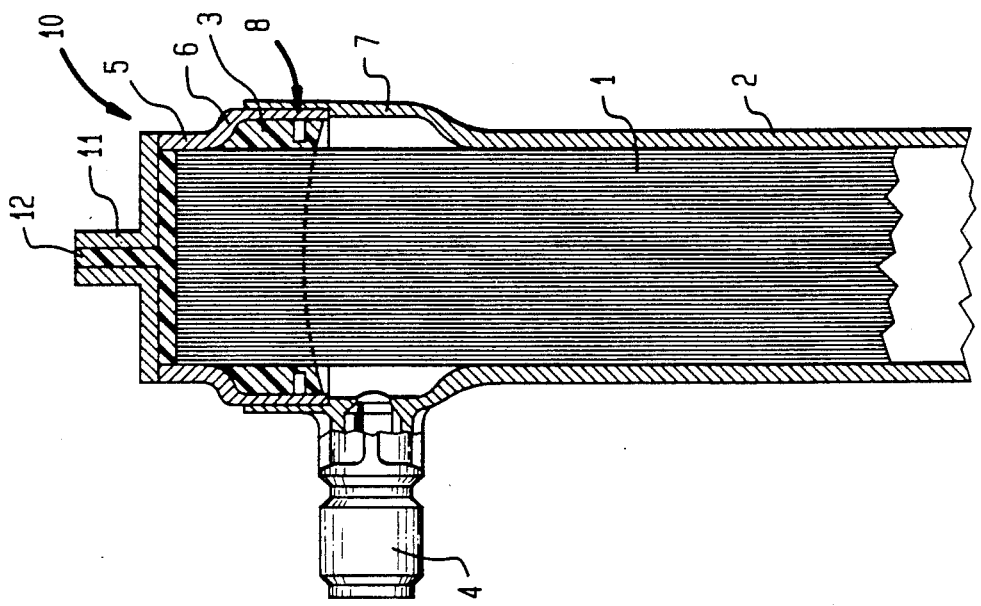
FIG. 2 is a partial, side, elevational, partially sectional view of the apparatus of FIG. 1 at a second stage of its manufacture.
Figure 1:
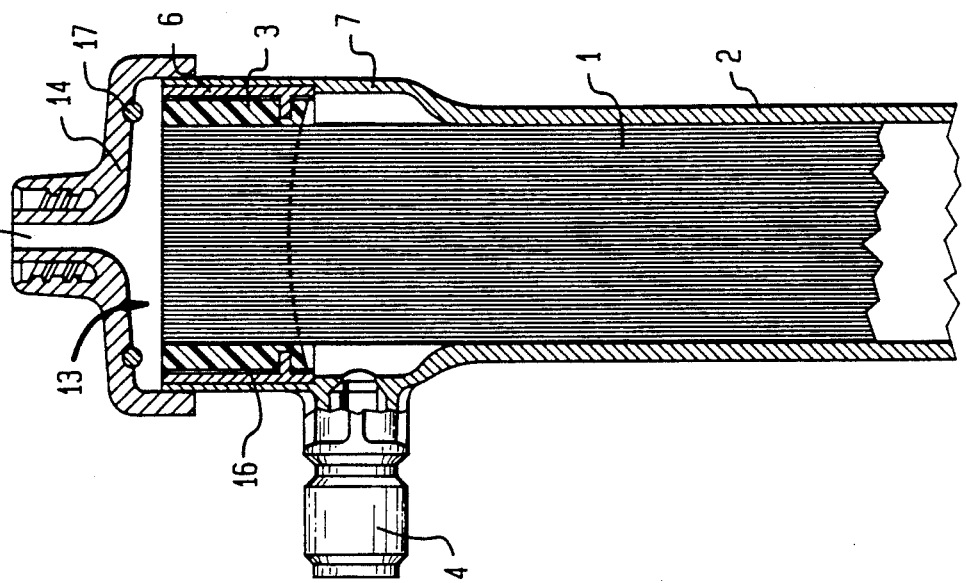
FIG. 1 is a partial, side, elevational, partially sectional view of a diffusion and/or filtration apparatus of the present invention at a first stage of its manufacture.

Referring to the figures, in which like reference numerals refer to like portions thereof, FIGS. 1 through 3 depict one end of an apparatus according to the present invention during three different phases of its manufacture.

In FIG. 1, a bundle of hollow fibers 1 is shown in a housing 2 prior to the casting of the end walls 3, (shown in FIGS. 2 and 3). The housing is provided with an inlet and/or outlet 4 which is intended for a first fluid. A similar inlet and/or outlet may be arranged at the other end of the device (not shown). The bundle of hollow fibers 1 is supported by a narrow portion 5 of ring 6 which is arranged in an expanded part 7 of the housing 2. The ring 6 is engaged in a groove 8 in the expanded part 7 of the housing 2. The ring 6 is provided with an inwardly extending flange 9 which is shown to reach to a point near the bundle of hollow fibers. Alternatively, it may reach up to the outermost hollow fibers in order to provide a secondary support for the bundle.

The ring 6 has, as mentioned above, a low coefficient of adhesion in relation to the material of the end walls 3. It may for instance be made of polypropylene when the end walls are made of polyurethane, which is a material commonly used for such end walls. Alternatively, the ring 6 may be made of polyethylene, preferably low density polyethylene (LDPE), a material which is easier to cut, or Teflon (polytetrafluorethylene), a material having a very low adhesive capacity as regards most other materials.

In FIG. 2, a mold 10 has been provided. Thus, ring 6 has been connected to a lid 11, having an inlet 12 for the end wall potting material.

Referring next to FIG. 3, end surface 13 has been created by transversively cutting through the bundle of hollow fibers 1, the housing 2, the end wall 3, and the ring 6. The apparatus has thereafter been provided with a lid 14 with an inlet and/or outlet 15 intended for a second fluid which may be fed through the fibers to a similar inlet and/or outlet 15 arranged at the opposite end of the apparatus (not shown).

Due to the relationship between the material of the end wall 3 and the ring 6, a small gap 16 has been provided therebetween. A sealing ring 17 has therefore been provided between the lid 14 and the end surface 13 in order to provide an effective seal between the two fluids involved, i.e., the fluids inside and outside the hollow fibers. It is to be observed that the gap 16 is not necessary. In practice, it is sufficient to reduce the degree of attachment between the end wall 3 and the ring 6. In order to prevent leakage, the lid 14 is preferably tightly welded to the outer surface of the expanded part 7 of the housing. Other methods of sealings are acceptable.

FIGS. 4 through 6 show a second embodiment of the apparatus according to the present invention. Many details are identical or similar to those shown in FIGS. 1 through 3, and have therefore been given the same reference numerals, but with the addition of an a.

Consequently, the apparatus as shown is made up of a bundle of hollow fibers 1a in a housing 2a having an expanded part 7a. In a groove 8a in the expanded part 7a, a slightly modified ring 6a is inserted. Ring 6a, as the previously described ring 6, is provided with a restricted part 5a supporting the bundle of hollow fibers 1a. Similarly, an inlet 4a corresponds to the previously described inlet 4.

The main difference between the embodiment according to FIGS. 4 through 6 and the above described embodiment, is a number of fingers or tongues 18a arranged in the expanded part 7a of the housing 2a. These fingers or tongues 18a are integral extensions of the inner wall of the housing 2a.

Referring next to FIG. 5, the ring 6a has been completed with a lid 11a, which includes an opening 12a for the casting material which make up the end walls 3a. The fingers or tongues 18a are, as can be seen in this figure, partly embedded in the end walls 3a. Thus, the tongues 18a provide support for the end walls 3a in the longitudinal direction of the housing 2a.

In FIG. 6 the bundle of hollow fibers 1a, the end wall 3a, the ring 6a and the expanded part 7a of the housing 2a have been transversely cut, providing an end surface 13a. The apparatus has furthermore been provided with a lid 14a with an inlet and/or outlet 15a and a sealing ring 17a.

FIGS. 7 through 9 and 9a show a preferred third embodiment of the apparatus according to the present invention. Many of the details shown are identical to or similar to the details of FIGS. 1 through 6 and have therefore been given the same reference numerals, but with the addition of b.

Accordingly, a bundle of hollow fibers 1b is arranged in a housing 2b provided with an expanded part 7b with an inlet and/or outlet 4b. A first ring 6b, similar to the ring 6 previously described, is arranged in a groove 8b in the expanded part 7b of the housing 2b. The ring 6b is provided with an inner flange 9b.

The main difference between the embodiment described in FIGS. 7 through 9 and 9a, and the embodiment shown in FIGS. 1 through 3, is a second ring 19b arranged partly outside the expanded part 7b of the housing 2b. Said second ring 19b is provided with a restricted part 5b which corresponds to the part 5 of the ring 6, and additionally, an inner longitudinal extending flange 20b which is intended to be partly embedded in the end wall 3b.

In FIG. 8, the ring 19b has been provided with a lid 11b which includes an opening 12b for the feeding of the casting material for the end walls 3b.

In FIG. 9, and the enlargement of a portion of the housing 2b, shown in FIG. 9a, the expanded part 7b of the housing 2b, the end wall 3b, the flange 20b and bundle of hollow fibers 1b, have been cut through, thus providing an end surface 13b. The apparatus has thereafter been provided with a lid 14b, which includes an opening 15b, and with a sealing ring 17b as described above.

Due to the fact that the ring 6b does not extend up to the end surface 13b, the material of the end wall 3b therefore attaches to the inside of the expanded part 7b of the housing 2b. This attachment provides a seal between the end of the housing 2b and the internal chamber of the housing. Therefore, the lid 14b does not have to be tightly attached to the outside wall of the expanded part 7b of the housing 2b. It may for instance, be attached to the housing 2b by means of a thread arranged between the lid 14b and the expanded part 7b.

The present invention also relates to a method of manufacturing a diffusion and/or filtration apparatus in accordance with the present invention. Specifically, referring to FIGS. 1 through 3, a housing 2 is provided which consists of a cylindrical open ended main part, closed by two end caps 14 and being provided with an inlet 15 and an outlet (not shown) for a first fluid and at least one additional outlet 4 for a second fluid. The first fluid is adapted to flow through the fibers 1 of a bundle of semi-permeable hollow fibers arranged between two end walls 3 within the housing 2, and the second fluid is adapted to be removed from the space outside the fibers through the additional outlet 4. The ends of the hollow fibers 1 are moulded into the end walls 3 and opened by transversely cutting same.

The method according to the invention includes the steps of arranging a bundle of semipermeable hollow fibers 1 in the cylindrical open ended main part of the housing 2. A ring 6 which has a low adhesive capacity in relation to the material of the end walls 3 is provided, and extends outside the open ends of the hollow fibers 1, and serves as an inlet and/or outlet for a flushing fluid for the flushing of the inside and the outside of the fibers 1. Additionally, ring 6 is thereafter used as a part of a mold for molding the end walls 3. Subsequently, the entire structure is cut in order to open the fiber ends, whereupon the apparatus finally is provided with end caps 14. Such may also include the additional steps as set forth in copending U.S. patent application No. 07/565,032.

Specifically, manufacturing such a diffusion/filtration apparatus comprises the steps of:

Providing a bundle of semi-permeable hollow fibers, the bundle of hollow fibers having a first end and a second end; providing a housing which defines a longitudinally extending internal chamber including a first open end and a second open end; inserting the bundle of hollow fibers into the internal chamber; providing a first ring member and inserting the ring member into at least one of the first and second open ends of the internal chamber between the housing and the bundle of hollow fibers; and providing a second ring member and affixing the second ring member to the housing. This second ring member extends beyond the hollow fibers and forms an inlet, and includes a longitudinally extending surface which extends a predetermined distance within the internal chamber between the housing and the hollow fibers. A predetermined quantity of a potting material, which when set has a lower coefficient of adhesion with respect to the housing means, is then inserted into the first and second open ends of the housing so as to penetrate into the internal chamber a first predetermined distance and into the hollow fibers a second predetermined distance. In this manner, the potting material seals the internal chamber from the ends of the hollow fibers. The housing, the first ring member, the second ring member and the hollow fibers are then cut transverse to the internal chamber at a predetermined point between the first and second predetermined distances so as to open the hollow fibers and provide an end wall supporting the ends of the hollow fibers. Lid means are then attached over the first and second ends of the housing.

All the above described figures show one end of the apparatus according to the invention. Normally the opposite end is identical to the end shown in the drawings. This is true when, for example, the apparatus is intended to be used for dialysis; a treatment which needs an inlet, as well as an outlet, for the dialysis liquid. If, however, the apparatus is intended to be used for filtration only, it is enough to have only one outlet for the filtrate.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A diffusion/filtration apparatus comprising:
   a) housing means, said housing means defining a longitudinally extending internal chamber including a first end and a second end;
   b) a bundle of semi-permeable hollow fibers disposed within said internal chamber, said hollow fibers extending longitudinally from said first end of said housing to said second end of said housing, said hollow fibers having an outer surface, and a first end and a second end corresponding to said first end and said second end of said internal chamber;
   c) end wall means supporting said first and second ends of said hollow fibers within said internal chamber so as to sealingly separate said first and second ends of said hollow fiber from said outer surface of said hollow fiber between said first and second ends thereof;
   d) first inlet means for the introduction of a fluid into said first end of said housing means;
   e) first outlet means for the evacuation of a fluid from said second end of said housing means;
   f) second outlet means for the evacuation of a fluid from said internal chamber at a location between said first and second end of said housing means;
   g) at least one ring member disposed between said end wall means and said housing means at one of said first and second ends of said internal chamber, said ring member being in direct contact with said housing and having a shape corresponding to said housing and defining a cavity between said ring member and said hollow fibers, the coefficient of adhesion between said end wall means and said ring member being lower than the coefficient of adhesion between said end wall means and said housing, whereby the structural integrity of said housing means and the seal between said ends of said hollow fibers and said outer surface of said hollow fibers is enhanced; and
   h) at least one sealing ring interposed between said end wall and said first inlet means.

2. The apparatus according to claim 1 including support means within said cavity for longitudinally supporting said end wall means.

3. The apparatus according to claim 2 wherein said ring member includes an inner surface and an outer surface, and wherein said support means comprise a flange extending inwardly from said inner surface of said ring member.

4. The apparatus according to claim 3 wherein said flange extends inwardly as to said bundle of hollow fibers so as to provide support therefor.

5. The apparatus according to claim 2 wherein said support means are integral with said housing.

6. The apparatus according to claim 5 wherein said support means comprise longitudinally extending tongue means extending from a predetermined location on said housing means between said first and second ends thereof into said end wall means.

7. The apparatus according to claim 2 including ring support means for supporting said ring member from said housing.

8. The apparatus according to claim 7 wherein said ring support means comprises an annular groove in said housing, said ring member being longitudinally engaged in said annular groove.

9. The apparatus according to claim 7 wherein said ring member includes an inner surface and an outer surface, and wherein said support means comprises a flange extending inwardly from said inner surface of said ring member.

10. The apparatus according to claim 1 wherein said first inlet means is defined by a first end cap covering said first end of said housing and said first outlet means is defined by a second end cap covering said second end of said housing.

11. The apparatus according to claim 10 wherein said first and second end caps are applied to said first and second ends of said housing by a means selected from the group consisting of welding and gluing.

12. A diffusion/filtration apparatus comprising:
   a) housing means, said housing means defining a longitudinally extending internal chamber including a first end and a second end;
   b) a bundle of semi-permeable hollow fibers disposed within said internal chamber, said hollow fibers extending longitudinally from said first end of said housing to said second end of said housing, said hollow fibers having an outer surface, and a first end and a second end corresponding to said first end and said second end of said internal chamber;
   c) end wall means supporting said first and second ends of said hollow fibers within said internal chamber so as to sealingly separate said first and second ends of said hollow fiber from said outer surface of said hollow fiber between said first and second ends thereof;
   d) first inlet means for the introduction of a fluid into said first end of said housing means, said first inlet means being defined by a first end cap covering said first end of said housing;
   e) first outlet means for the evacuation of a fluid from said second end of said housing means, said first outlet means being defined by a second end cap covering said second end of said housing, said first and second end caps being applied to said first and second ends of said housing in a fluid-tight manner;
   f) second outlet means for the evacuation of a fluid from said internal chamber at a location between said first and second end of said housing means; and
   g) at least one ring member disposed between said end wall means and said housing means at one of said first and second ends of said internal chamber, said ring member being in direct contact with said housing and having a shape corresponding to said housing and defining a cavity between said ring member and said hollow fibers, the coefficient of adhesion between said end wall means and said ring member being lower than the coefficient of adhesion between said end wall means and said housing, whereby the structural integrity of said housing means and the seal between said ends of said hollow fibers and said outer surface of said hollow fibers is enhanced.

13. The apparatus according to claim 12 including support means within said cavity for longitudinally supporting said end wall means.

14. The apparatus according to claim 13 wherein said ring member includes an inner surface and an outer surface, and wherein said support means comprise a flange extending inwardly from said inner surface of said ring member.

15. The apparatus according to claim 14 wherein said flange extends inwardly as to said bundle of hollow fibers so as to provide support therefor.

16. The apparatus according to claim 13 wherein said support means are integral with said housing.

17. The apparatus according to claim 16 wherein said support means comprise longitudinally extending tongue means extending from a predetermined location on said housing means between said first and second ends thereof into said end wall means.

18. The apparatus according to claim 13 including ring support means for supporting said ring member from said housing.

19. The apparatus according to claim 18 wherein said ring support means comprises an annular groove in said housing, said ring member being longitudinally engaged in said annular groove.

20. The apparatus according to claim 12 including at least one sealing ring interposed between said end wall and said first inlet means.

21. A diffusion/filtration apparatus comprising:
   a) housing means, said housing means defining a longitudinally extending internal chamber including a first end and a second end;
   b) a bundle of semi-permeable hollow fibers disposed within said internal chamber, said hollow fibers extending longitudinally from said first end of said housing to said second end of said housing, said hollow fibers having an outer surface, and a first end and a second end corresponding to said first end and said second end of said internal chamber;
   c) end wall means supporting said first and second ends of said hollow fibers within said internal chamber so as to sealingly separate said first and second ends of said hollow fiber from said outer surface of said hollow fiber between said first and second ends thereof;
   d) first inlet means for the introduction of a fluid into said first end of said housing means;
   e) first outlet means for the evacuation of a fluid from said second end of said housing means;
   f) second outlet means for the evacuation of a fluid from said internal chamber at a location between said first and second end of said housing means; and
   g) at least one ring member disposed between said end wall means and said housing means at one of said first and second ends of said internal chamber, so as to prevent contact between said end wall means and said housing means, said ring member having a shape corresponding to said housing and defining a cavity between said ring member and said hollow fibers, the coefficient of adhesion between said end wall means and said ring member being lower than the coefficient of adhesion between said end wall means and said housing, whereby the structural integrity of said housing means and the seal between said ends of said hollow fibers and said outer surface of said hollow fibers is enhanced.

22. The apparatus according to claim 21, including support means within said cavity for longitudinally supporting said end wall means.

23. The apparatus according to claim 22 wherein said support means are integral with said housing.

24. The apparatus according to claim 23 wherein said support means comprise longitudinally extending tongue means extending from a predetermined location on said housing means between said first and second ends thereof into said end wall means.

25. The apparatus according to claim 22 including ring support means for supporting said ring member from said housing.

26. The apparatus according to claim 25 wherein said ring support means comprises an annular groove in said housing, said ring member being longitudinally engaged in said annular groove.

27. The apparatus according to claim 25 wherein said ring member includes an inner surface and an outer surface, and wherein said support means comprises a flange extending inwardly from said inner surface of said ring member.

28. The apparatus according to claim 27 including at least one sealing ring interposed between said end wall and said first inlet means.

29. The apparatus according to claim 21 wherein said ring member includes an inner surface and an outer surface, and wherein said support means comprise a flange extending inwardly from said inner surface of said ring member.

30. The apparatus according to claim 29 wherein said flange extends inwardly as to said bundle of hollow fibers so as to provide support therefor.

31. The apparatus according to claim 21 wherein said first inlet means is defined by a first end cap covering said first end of said housing and said first outlet means is defined by a second end cap covering said second end of said housing.

32. The apparatus according to claim 31 wherein said first and second end caps are applied to said first and second ends of said housing by a means selected from the group consisting of welding and gluing.

33. A diffusion/filtration apparatus comprising:
   a) housing means, said housing means defining a longitudinally extending internal chamber including a first end and a second end;
   b) a bundle of semi-permeable hollow fibers disposed within said internal chamber, said hollow fibers extending longitudinally from said first end of said housing to said second end of said housing, said hollow fibers having an outer surface, and a first end and a second end corresponding to said first end and said second end of said internal chamber;
   c) end wall means supporting said first and second ends of said hollow fibers within said internal chamber so as to sealingly separate said first and second ends of said hollow fiber from said outer surface of said hollow fiber between said first and second ends thereof;
   d) first inlet means for the introduction of a fluid into said first end of said housing means;
   e) first outlet means for the evacuation of a fluid from said second end of said housing means;
   f) second outlet means for the evacuation of a fluid from said internal chamber at a location between said first and second end of said housing means;
   g) at least one ring member disposed between said end wall means and said housing means at one of said first and second ends of said internal chamber, said ring member having a shape corresponding to said housing and defining a cavity between said ring member and said hollow fibers, the coefficient of adhesion between said end wall means and said ring member being lower than the coefficient of adhesion between said end wall means and said housing, whereby the structural integrity of said housing means and the seal between said ends of said hollow fibers and said outer surface of said hollow fibers is enhanced; and h) support means integral for said housing, said support means comprising longitudinally extending tongue means extending from a predetermined location on said housing means between said first and second ends thereof into said end wall means for longitudinally supporting said end wall means.

34. The apparatus according to claim 33 including ring support means for supporting said ring member from said housing.

35. The apparatus according to claim 34 wherein said ring support means comprises an annular groove in said housing, said ring member being longitudinally engaged in said annular groove.

36. The apparatus according to claim 33 wherein said first inlet means is defined by a first end cap covering said first end of said housing and said first outlet means is defined by a second end cap covering, said second end of said housing.

37. The apparatus according to claim 36 wherein said first and second end caps are applied to said first and second ends of said housing by a means selected from the group consisting of welding and gluing.

38. The apparatus according to claim 33 including at least one sealing ring interposed between said end wall and said first inlet means.

39. A diffusion/filtration apparatus comprising:
a) housing means, said housing means defining a longitudinally extending internal chamber including a first end and a second end;
b) a bundle of semi-permeable hollow fibers disposed within said internal chamber, said hollow fibers extending longitudinally from said first end of said housing to said second end of said housing, said hollow fibers having an outer surface, and a first end and a second end corresponding to said first end and said second end of said internal chamber;
c) end wall means supporting said first and second ends of said hollow fibers within said internal chamber so as to sealingly separate said first and second ends of said hollow fiber from said outer surface of said hollow fiber between said first and second ends thereof;
d) first inlet means for the introduction of a fluid into said first end of said housing means;
e) first outlet means for the evacuation of a fluid from said second end of said housing means;
f) second outlet means for the evacuation of a fluid from said internal chamber at a location between said first and second end of said housing means;
g) at least one ring member disposed between said end wall means and said housing means at one of said first and second ends of said internal chamber, said ring member having a shape corresponding to said housing and defining a cavity between said ring member and said hollow fibers, the coefficient of adhesion between said end wall means and said ring member being lower than the coefficient of adhesion between said end wall means and said housing, whereby the structural integrity of said housing means and the seal between said ends of said hollow fibers and said outer surface of said hollow fibers is enhanced; and h) support means within said cavity for longitudinally supporting said end wall means.

40. The apparatus according to claim 39 wherein said ring member includes an inner surface and an outer surface, and wherein said support means comprise a flange extending inwardly from said inner surface of said ring member.

41. The apparatus according to claim 40 wherein said flange extends inwardly as to said bundle of hollow fibers so as to provide support therefor.

42. The apparatus according to claim 39 wherein said support means are integral with said housing.

43. The apparatus according to claim 42 wherein said support means comprise longitudinally extending tongue means extending from a predetermined location on said housing means between said first and second ends thereof into said end wall means.

44. The apparatus according to claim 39 wherein said first inlet means is defined by a first end cap covering said first end of said housing and said first outlet means is defined by a second end cap covering said second end of said housing.

45. The apparatus according to claim 44 wherein said first and second end caps are applied to said first and second ends of said housing by a means selected from the group consisting of welding and gluing.

46. The apparatus according to claim 39 including at least one sealing ring interposed between said end wall and said first inlet means.

47. A diffusion/filtration apparatus comprising:
a) housing means, said housing means defining a longitudinally extending internal chamber including a first end and a second end;
b) a bundle of semi-permeable hollow fibers disposed within said internal chamber, said hollow fibers extending longitudinally from said first end of said housing to said second end of said housing, said hollow fibers having an outer surface, and a first end and a second end corresponding to said first end and said second end of said internal chamber;
c) end wall means supporting said first and second ends of said hollow fibers within said internal chamber so as to sealingly separate said first and second ends of said hollow fiber from said outer surface of said hollow fiber between said first and second ends thereof;
d) first inlet means for the introduction of a fluid into said first end of said housing means;
e) first outlet means for the evacuation of a fluid from said second end of said housing means; wherein said support means comprise a flange extending inwardly from said inner surface of said ring member;
f) second outlet means for the evacuation of a fluid from said internal chamber at a location between said first and second end of said housing means; and
g) at least one ring member disposed between said end wall means and said housing means at one of said first and second ends of said internal chamber, said ring member having a shape corresponding to said housing and defining a cavity between said ring member and said hollow fibers, said ring member being in direct contact with said housing means, and said end wall means at said one of said first and second ends of said internal chamber having a first portion in contact with said ring member comprising a substantial portion of said end wall means, and having a second portion comprising a minor portion of said end wall means engaging said housing means between said one of said first and second ends of said internal chamber and said at least one ring member, said end wall means including slot means therein at a location adjacent to said second portion of said end wall means, the coefficient of adhesion between said first portion of said end wall means and said ring member being lower than the coefficient of adhesion between said second portion of said end wall means and said housing, whereby the structural integrity of said housing means and the seal between said ends of said hollow fibers and said outer surface of said hollow fibers is enhanced, while at the same time a seal is provided between said at least one of said first and second ends of said internal chamber and said internal chamber.

48. The apparatus according to claim 47 including support means within said cavity for longitudinally supporting said end wall means.

49. The apparatus according to claim 48 wherein said ring member includes a inner surface and an outer surface, and 50. The apparatus according to claim 47 including at least one sealing ring interposed between said end wall and said first inlet means.

* * * * *

UNITED STATES PATENT AND TRADEMARK OFFICE
CERTIFICATE OF CORRECTION

PATENT NO. : 5,053,130
DATED : October 1, 1991
INVENTOR(S) : Manfred Raff and Kurt Spranger It is certified that error appears in the above-identified patent and that said Letters Patent is hereby corrected as shown below:

```
Column 6, line 10, following "fibers" insert --1--.
Column 12, lines 55 through 58, delete "wherein said support
means comprise a flange extending inwardly from said inner
surface of said ring member;".
Column 14, line 12, following "and" insert --wherein said
support means comprise a flange extending inwardly from said
inner surface of said ring member.--
```

Signed and Sealed this

Ninth Day of November, 1993

*Attest:*

BRUCE LEHMAN

*Attesting Officer*    Commissioner of Patents and Trademarks